United States Patent [19]

Cooper et al.

[11] Patent Number: 4,764,519

[45] Date of Patent: Aug. 16, 1988

[54] 3-HYDROXYPYRIDINES

[75] Inventors: David G. Cooper, Letchworth; Peter D. Miles, Lower Stondon; Rodney C. Young, Hertford, all of England

[73] Assignee: Smith Kline & French Laboratories Limited, Welwyn Garden City, England

[21] Appl. No.: 45,106

[22] Filed: May 1, 1987

[30] Foreign Application Priority Data

May 2, 1986 [GB] United Kingdom ............... 8610867

[51] Int. Cl.[4] ................... C07D 401/14; A61K 31/44
[52] U.S. Cl. .................... 514/335; 546/261; 546/21; 546/176; 546/112; 514/314
[58] Field of Search ............ 546/261, 21; 514/335

[56] References Cited

U.S. PATENT DOCUMENTS

| 4,374,248 | 2/1983 | Crenshaw et al. | 548/135 |
| 4,444,772 | 4/1984 | Sach | 544/320 |
| 4,471,122 | 9/1984 | Crenshaw et al. | 546/209 |
| 4,486,434 | 12/1984 | Sach | 544/320 |
| 4,532,252 | 7/1985 | Sach | 514/357 |
| 4,537,890 | 8/1985 | Sach | 514/272 |
| 4,537,891 | 8/1985 | Sach | 514/272 |

FOREIGN PATENT DOCUMENTS

0040696 12/1981 European Pat. Off. .

*Primary Examiner*—Jane T. Fan
*Attorney, Agent, or Firm*—Linda E. Hall; Janice E. Williams; Alan D. Lourie

[57] ABSTRACT

The disclosure relates to a class of 2-(pyridylalkylamino)-3-hydroxypyridines which are active as histamine $H_1$-antagonists.

10 Claims, No Drawings

3-HYDROXYPYRIDINES

This invention relates to certain pyridine derivatives, a process for their preparation, compositions containing them and their use as histamine $H_1$-antagonists.

Histamine, a physiologically active compound endogenous in mammals, exerts its action by interacting with certain sites called receptors. One type of receptor is known as a histamine $H_1$-receptor (Ash and Schild, Brit. J. Pharmac. 1966, 27, 427) and the actions of histamine at these receptors are inhibited by drugs commonly called "antihistamines" (histamine $H_1$-antagonists) a common example of which is mepyramine.

According to the present invention there are provided compounds of formula (1):

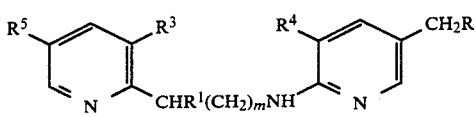

and pharmaceutically acceptable acid addition salts thereof in which
   $R^1$ is hydrogen or can together with $R^3$ form a —$(CH_2)_n$— group where n is 2, 3 or 4;
   $R^3$ is hydrogen, $C_{1-4}$alkyl, halogen, or amino, or $R^3$ together with $R^1$ can form a —$(CH_2)_n$— group;
   $R^4$ is hydroxy or a phosphate group;
   $R^5$ is hydrogen, $C_{1-4}$alkyl, halogen, or amino, provided that $R^3$ and $R^5$ are not both hydrogen;
   m is 2, 3 or 4; and
   R is a 2, 3, or 4-pyridyl or pyridyl N-oxide or N-$C_1$-$C_4$alkylpyridone group optionally substituted by one or two groups selected from $C_{1-4}$alkyl, $C_{1-4}$alkoxy, hydroxy and hydroxymethyl.

Examples of alkyl groups for $R^3$, $R^5$ and the optional substituents in R are methyl, ethyl and n-propyl.

Examples of alkoxy groups for the optional substituents in R are methoxy, ethoxy and n-propoxy.

Examples of halogen atoms for $R^3$ and $R^5$ are fluorine, chlorine, bromine and iodine.

Examples of phosphate groups $R^4$ are groups having the general formula:

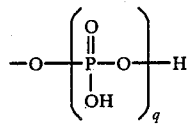

wherein q is 1 to 3. Preferably q is 1.

A first class of compounds of formula (1) in which $R^1$ is hydrogen is illustrated by formula (2):

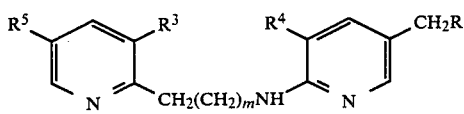

in which $R^3$, $R^4$, $R^5$, m and R are as defined for formula (1).

In this class of compound preferably the substituents have the following meanings: $R^3$ is halogen, alkyl or amino, $R^5$ is hydrogen, halogen or alkyl, and m is 3. Particularly $R^3$ is alkyl (especially methyl) or amino and $R^5$ is halogen (especially bromine) or alkyl (especially methyl). Particularly preferred meanings for combinations of $R^3$ and $R^5$ are $R^3$ is methyl or amino and $R^5$ is bromine.

A second class of compounds of formula (1) in which $R^1$ and $R^3$ together form a —$(CH_2)_n$— is illustrated by formula (3):

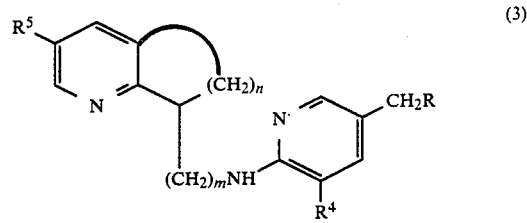

in which $R^4$, $R^5$, n, m and R are as defined for formula (1). For this class of compound preferably $R^5$ is hydrogen or halogen (particularly bromine), particularly preferably hydrogen, and n is 3, and m is 3.

For both the compounds of formula (2) and formula (3) preferably R is 3- or 4-pyridyl or pyridyl-N-oxide optionally substituted by methyl, hydroxymethyl or methoxy.

Particularly preferably R is 3-pyridyl, 6-methyl-3-pyridyl, 6-methyl-3-pyridyl N-oxide or 6-hydroxymethyl-3-pyridyl.

Examples of preferred compounds of formula (1) are:
2-[4-(5-bromo-3-methylpyrid-2-yl)butylamino]-3-hydroxy-5-(pyrid-3-ylmethyl)pyridine,
2-[3-(5-bromo-3-methylpyrid-2-yl)propylamino]-3-hydroxy-5-(pyrid-3-ylmethyl)pyridine,
2-[4-(5-bromo-3-methylpyrid-2-yl)butylamino]-3-hydroxy-5-(6-hydroxymethyl-pyrid-3-ylmethyl)pyridine,
2-[3-(5,6,7,8-tetrahydroquinol-8-yl)propylamino]-3-hydroxy-5-(pyrid-3-ylmethyl)pyridine,
2-[2-(5,6,7,8-tetrahydroquinol-8-yl)ethylamino]-3-hydroxy-5-(pyrid-3-ylmethyl)pyridine, and
2-[4-(5-bromo-3-methylpyrid-2-yl)butylamino]-5-(pyrid-3-ylmethyl)pyrid-3-yloxyphosphate.

The compounds of formula (1) wherein $R^4$ is hydroxy can exist in the zwitterionic forms, particularly when in aqueous solution.

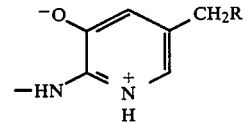

The compounds of formula (1) in which R is pyridyl substituted by hydroxy can also exist in tautomeric dihydropyridone forms. All such tautomers and zwitterionic forms are included within the scope of this invention.

The compounds of formula (3) exhibit optical isomerism and the present invention covers both optical isomers of these compounds in racemic and resolved states.

Solvates of compounds of the formula (1) and their salts, for example hydrates and alcoholates, are also within the scope of the present invention.

The compounds of formula (1) can be prepared from a 3-aminopyridyl derivative of formula (4):

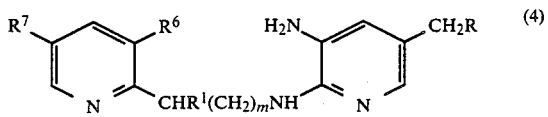  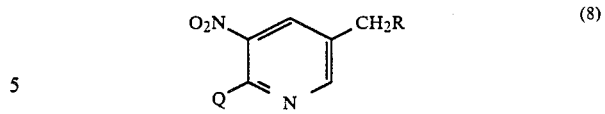

in which $R^6$ and $R^7$ have the same meanings as $R^3$ and $R^5$ in formula (1) except that any amino group present must be protected with an amino-protecting group which is stable under mild acidic conditions, and $R^1$, m and R are as defined for formula (1). Examples of amino-protecting groups which are stable under mild acidic conditions are well known to the art, see for example "Protective Groups in Organic Synthesis", T. W. Greene, 1981 (Wiley), and acetyl and benzoyl are specific examples.

Suitably the compounds of formula (4) are diazotised to give a triazolopyridine of formula (5):

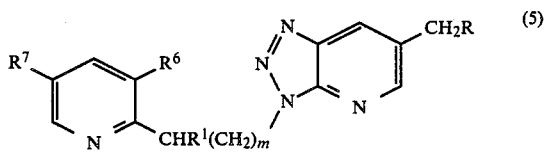

in which R, $R^1$, $R^6$, $R^7$ and m are as defined for formula (4). Suitably this diazotisation is carried out under acidic conditions. Suitably the diazotisation is carried out using sodium nitrite in aqueous acid, e.g. dilute sulphuric acid.

The triazolopyridine of formula (5) can be hydrolytically decomposed to give the compound of formula (1) wherein $R^4$ is hydroxy with deprotection of any amino-protecting groups present. Suitably this reaction is carried out in polyphosphoric acid. Suitably the reaction is carried out at a temperature of 150° to 250° C., preferably 190° to 210° C.

The amines of formula (4) can be prepared by reducing a nitro compound of formula (6):

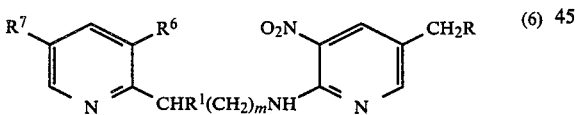

in which R, $R^1$ and m are as defined for formula (1) and $R^6$ and $R^7$ are as defined for formula (4). When $R^6$ or $R^7$ are halogen a selective reducing agent will be necessary, for example hydrazine and Raney nickel, or stannous chloride.

The nitro compounds of formula (6) can be prepared by reacting an amine of formula (7):

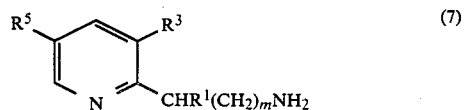

in which $R^1$, $R^3$, $R^5$ and m are as defined for formula (1), except that when $R^3$ and/or $R^5$ are amino groups, these are optionally protected; with a compound of formula (8):

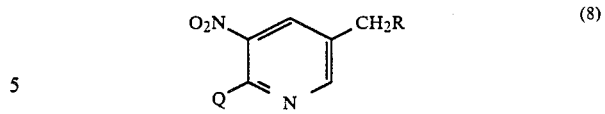

in which R is as defined for formula (1) and Q is a leaving group displaceable with an amine; and thereafter, when $R^3$ and/or $R^5$ are unprotected amino, reacting these with a reagent suitable for introducing an amino protecting group. Examples of leaving groups displaceable with an amine are halogen, $C_{1-4}$alkylthio, and $C_{1-4}$alkoxy. Preferably Q is chlorine. Preferably the reaction is carried out in the absence of a solvent or in dipolar protic or dipolar aprotic solvent at an elevated temperature. Examples of protic solvents are $C_{1-4}$alkanols and examples of dipolar aprotic solvents are dimethylformamide, dimethylsulphoxide, pyridine, picolines and anisole. Preferably the reaction is carried out in ethanol at the reflux temperature of the reaction mixture. Preferably when Q is halogen an excess of a non-nucleophilic base is added. Examples of non-nucleophilic bases are pyridine and triethylamine.

The compounds of formula (8) in which Q is chlorine can be prepared by reacting a compound of formula (9):

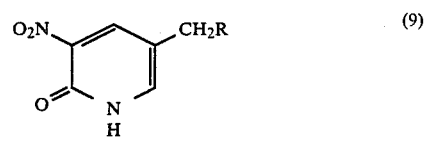

in which R is as defined for formula (1), with a chlorinating agent. Preferably the chlorinating agent is phosphoryl chloride. The compounds of formula (8) in which Q is other than chlorine can be prepared from the compounds of formula (8) in which Q is chlorine or in the case of Q being alkylthio by reacting a compound of formula (9) with a thionating reagent such as phosphorus pentasulphide and alkylating the product.

The intermediates of formula (9) can be made by processes described in the Examples and processes analogous thereto.

The amines of formula (7) in which $R^3$ and $R^1$ together form a $-(CH_2)_n-$ group and in which $R^5$ is other than halogen can be prepared by reacting a compound of formula (10):

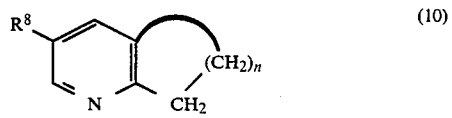

where $R^8$ is hydrogen, $C_{1-4}$alkyl, nitro or protected amino, and n is 2, 3 or 4, with a compound of formula (11):

where m is as defined with reference to formula (1), X is halogen, $R^9$ is amino or a protected amino group, in the presence of a strong base and thereafter removing any amino protecting group, and reducing any nitro group present.

Examples of strong bases are alkali metal hydrides, particularly sodium hydride. The reaction is carried out in the presence of a polar solvent for example dimethylsulphoxide. Preferably $R^9$ is amino and the reaction is carried out using sodamide in liquid ammonia.

In formula (11) X can be chlorine, bromine or iodine. Preferably X is chlorine when sodamide is the base.

The protected amino group can be converted into amino by standard methods, for example when it is phthalimido by reaction with concentrated hydrochloric acid or hydrazine.

Alternatively, the compounds of formula (10) can be reacted with an organolithium compound (e.g. phenyllithium or butyllithium) and subsequently reacted with a compound of formula (11). (See for example Aldrichimica Acta II, 15, (1978)).

The amines of formula (7) in which $R^3$ and $R^1$ together form a $-(CH_2)_n-$ group and in which $R^5$ is halogen can be prepared by carrying out a Sandmeyer reaction on a 3-amino compound of formula (12):

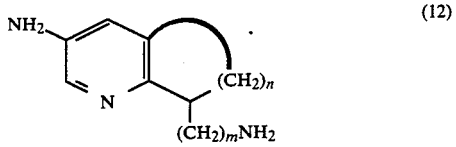

(in which m and n are as defined for formula (1)) that is by diazotisation of the aromatic amino group under strongly acidic conditions and displacing the resulting diazo group with halogen.

The amines of formula (7) in which $R^5$ is bromine can also be prepared by the direct bromination of the amines of formula (7) in which $R^5$ is hydrogen. Preferably the bromination is carried out with electrophilic bromine, for example using bromine in sulphuric acid.

The amines of formula (7) in which $R^1$ is hydrogen can be prepared by known methods, e.g. as described in EP 0068833.

Compounds of the formula (1) wherein $R^4$ is a phosphate group can be prepared, for example, by reaction of triazolopyridines of the formula (5) with polyphosphoric acid under conditions designed to minimise hydrolysis of the phosphate to the corresponding free hydroxy compound.

Phosphates can also be prepared from the corresponding 3-hydroxypyridine of the formula (1) wherein $R^4$ is hydroxy by methods known per se or analogous thereto, for example by reaction of the said 3-hydroxypyridine with the appropriate phosphorylhalide.

The histamine $H_1$-antagonist activity of the compounds of formula (1) can be demonstrated in vitro in the guinea pig ileum test. In this test an isolated portion of the guinea pig ileum is secured under tension (500 mg) between an anchorage and a transducer in a 10 ml tissue bath and immersed in magnesium free Tyrode solution with constant aeration at a temperature of 30° C. The output from the transducer is amplified. The amplified output is in turn fed to a flat bed recorder. Measured amounts of histamine are added to the tissue bath so that the histamine concentration increases stepwise until the force of the contraction reaches a maximum. The tissue bath is washed out and filled with fresh magnesium free Tyrode solution containing compound under test. The solution is left in contact with the tissue for 8 min. and measured amounts of histamine are added again until a maximum contraction is recorded. The assay is repeated with increasing concentrations of test compound and the dose of histamine giving 50% of maximum contraction is noted. A dose ratio (DR) was calculated by comparing the concentrations of histamine required to produce 50% maximum response in the absence and in the presence of the antagonist. A plot of Log DR-1 against Log D (the concentration of compound under test) is made and the point of intersection with the Log (Dr-1) ordinate is taken as the measure of the activity ($pA_2$ value).

The activity of compounds of formula (1) as histamine $H_1$-antagonists can be demonstrated in vivo by the inhibition of histamine induced bronchoconstriction. Guinea pigs of either sex are anaesthetised by intraperitoneal injection of sodium pentobarbitone, 90 mg/kg. The trachea is cannulated. The animal is respired artificially with a fixed volume of air just adequate to inflate the lungs. The pressure needed to inflate the lungs is monitored from the respiratory system using a pressure transducer. Intravenous injection of histamine causes dose-dependent increases in the pressure to inflate the lungs reflecting the bronchoconstrictor action of histamine. Responses to histamine can be antagonised using histamine $H_1$-receptor antagonists.

Dose-response curves to histamine are established at 2, 40, 80, 160 and 320 nmols/kg. Antagonists are then administered by intravenous injection and 5 minutes later a new histamine dose-response curve is established increasing the doses of histamine as necessary. The effect of the antagonist can be quantified by the displacement, to the right, of the histamine dose-response curve, expressed as a dose-ratio. A series of doses of antagonists may be given to each animal allowing calculation of dose-ratios for each dose of antagonist.

The biological activities of the compounds of the Examples are described in Table 1 below.

TABLE 1

| Compound of Example No. | $pA_2$ ileum | Guinea Pig bronchoconstriction DR-1 = 10 μm/kg |
|---|---|---|
| 1(h) | 8.71 | 0.016 |
| 2(e) | 8.02 | 0.038 |
| 3(h) | 8.82 | — |
| 1(i) | 8.09 | 0.033 |

In order to use the compounds of the invention as histamine $H_1$-antagonists, they can be formulated as pharmaceutical compositions in accordance with standard pharmaceutical procedure.

The invention also includes pharmaceutical compositions comprising a compound of formula (1) or a pharmaceutically acceptable salt thereof and a pharmaceutically acceptable carrier.

Compounds of formula (1) and their pharmaceutically acceptable salts can be administered topically or systemically.

Topical formulations for administration to the skin include lotions and creams. Topical formulations for administration to the respiratory tract include solutions for application via a nebulizer or as an aerosol, or a microfine insufflatable powder. The active ingredient in an insufflatable powder has a small particle size i.e. less than 50 microns and preferably less than 10 microns. The active material is co-presented with a solid carrier for example lactose which has a particle size of less than 50 microns.

Systemic administration can be achieved by rectal, oral or parenteral administration. A typical suppository formulation comprises the active compound with a binding agent and/or lubricating agent for example gelatine or cocoa butter or other low melting vegetable waxes or fats. Typical parenteral compositions consist of a solution or suspension of the active material in a sterile aqueous carrier or parenterally acceptable oil.

Compounds of formula (1) which are active when given orally can be formulated as syrups, tablets, capsules and lozenges. A syrup formulation generally consists of a suspension or solution of the compound in a liquid carrier for example ethanol, glycerine or water with a flavouring or colouring agent. Where the composition is in the form of a capsule, the solid in granular form optionally with a binding agent is encased in a gelatin shell. Where the composition is in the form of a tablet, any suitable pharmaceutical carrier routinely used for preparing solid formulations can be used. Examples of such carriers include magnesium stearate, starch, lactose, glucose, sucrose, and cellulose. Preferably the composition is in unit dose form for example a tablet, capsule or metered aerosol so that the patient may administer to himself a single dose.

Where appropriate, small amounts of bronchodilators and anti-asthmatics for example sympathomimetic amines particularly isoprenaline, isoetharine, salbutamol, phenylephrine and ephedrine; xanthine derivatives particularly theophylline and aminophylline; and corticosteroids particularly prednisolone and adrenal stimulants particularly ACTH can be included. As in common practice, the compositions will usually be accompanied by written or printed directions for use in the medical treatment concerned, in this case as a histamine $H_1$-antagonist for treatment of, for example, asthma, hayfever, rhinitis or allergic eczema.

Each dosage unit for oral administration contains preferably from 5 to 200 mg of a compound of formula (1) or a pharmaceutically acceptable salt thereof calculated as the free base.

The pharmaceutical compositions of the invention will normally be administered to a man for the treatment of rhinitis, hayfever, bronchial asthma or allergic eczema. An adult patient will receive an oral dose of between 15 mg and 400 mg and preferably between 15 mg and 200 mg or an intravenous, subcutaneous or intramuscular dose of between 1 mg and 50 mg, and preferably between 1 mg and 10 mg of a compound of formula (1) or a pharmaceutically acceptable salt thereof calculated as the free base, the composition being administered 1 to 4 times per day.

The following Examples illustrate the invention.

EXAMPLE 1

(a) 2-Methoxy-5-(pyrid-3-ylhydroxymethyl)pyridine

5-Bromo-2-methoxypyridine (188 g) was added over 30 minutes to a 1.55 molar solution of n-butyllithium in hexane (770 ml) and ether (1200 ml) stirred at −50° C. The suspension was stirred for 1 hour when pyridine-3-carboxaldehyde (112 g) in ether (200 ml) was added over 30 minutes. The solution was stirred for 3.5 hr and then allowed to warm to ambient temperature. Saturated ammonium chloride solution (100 ml) and water (2 L) was added and the solution was concentrated to ca. 2.5 L in vacuo. Chloroform (3 L) was added and the title compound (41.3 g) was collected by filtration. The chloroform layer was separated, dried over magnesium sulphate and the solvent was removed under reduced pressure. The residue was treated with chloroform (200 ml) and filtered to give a second crop of the product (51.01 g). Recrystallisation from isopropanol/ether gave the title compound, m.p. 129°–130° C.

$C_{12}H_{12}N_2O_2$: Requires: C, 66.65; H, 5.59; N, 12.96; Found: C, 66.56; H, 5.63; N, 13.09%

(b) 5-(Pyrid-3-ylmethyl)-2-pyridone

A solution of 2-methoxy-5-(pyrid-3-ylhydroxymethyl)pyridine (41 g) in acetic anhydride (150 ml) and pyridine (100 ml) was heated on a steam bath for 1 hour. The solvent was removed in vacuo and the residue was dissolved in ethanol (500 ml). The resulting solution was shaken with 10% palladium on carbon (4.6 g) under an atmosphere of hydrogen at 50 p.s.i. until uptake was complete. The catalyst was removed by filtration and the filtrate was treated with ethanol saturated with hydrogen chloride gas (300 ml). The solution was refluxed for 18 hours, cooled and the product collected by filtration to give the title compound as the dihydrochloride salt (37.0 g), m.p. 252°–254° C.

$C_{11}H_{10}N_2O.2HCl$: Requires: C, 50.98; H, 4.67; N, 10.81; Cl, 27.36%; Found: C, 50.88; H, 4.83; N, 10.66; Cl, 27.24%

5-(3-Pyridylmethyl)-2-pyridone dihydrochloride (36 g) was dissolved in water, basified with sodium hydroxide and extracted into chloroform (3×100 ml). The combined extracts were dried over magnesium sulphate and the solvent removed to give 5-(3-pyridylmethyl)-2-pyridone (26 g), m.p. 142°–144° C.

(c) 3-Nitro-5-(pyrid-3-ylmethyl)-2-pyridone 5-(Pyrid-3-ylmethyl)-2-pyridone (10 g) was added to concentrated sulphuric acid (20 ml) with cooling and stirring. Fuming nitric acid (4.5 ml) was then added over 10 mins. with cooling (ice-bath), allowed to warm to room temperature overnight and then poured on to ice (200 ml). Concentrated ammonium hydroxide solution was added to bring the pH to 8, when the product precipitated from solution. The solid was filtered off and recrystallised from methanol to give the title compound (7.04 g), m.p. 216°–7° C.

(d) 2-Chloro-3-nitro-5-(pyrid-3-ylmethyl)-2-pyridine

A mixture of 3-nitro-5-(pyrid-3-ylmethyl)-2-pyridone (32 g) and phosphorous oxychloride (120 ml) was refluxed with stirring for 3 hrs. The phosphorous oxychloride was then removed in vacuo and the residue was treated with chloroform/ether mixture. The solid produced was filtered off and recrystallised from ethanol/ether to give the title compound as a hydrochloride salt (28 g), m.p. 199°–200° C.

(e) 2-[4-(5-Bromo-3-methylpyrid-2-yl)butylamino]-3-nitro-5-(pyrid-3-ylmethyl)pyridine A mixture of 4-(5-bromo-3-methylpyrid-2-yl)butylamine (11.79 g) and 2-chloro-3-nitro-5-(pyrid-3-ylmethyl)pyridine hydrochloride (4.57 g) was refluxed in ethanol (100 ml) for 8 hours. The solvent was removed in vacuo, the residue was dissolved in water (100 ml) and then extracted with chloroform (100 ml). The chloroform extract was chromatographed on silica eluted with 5% v/v methanol in chloroform followed by recrystallisation from chloroform/hexane to give the title compound as a yellow solid, m.p. 82°–84° C.

(f)
3-Amino-2-[4-(5-bromo-3-methylpyrid-2-yl)butylamino]-5-(pyrid-3-ylmethyl)pyridine Hydrazine hydrate (5 ml) in methanol (25 ml) was added with stirring over 20 minutes to a cooled (10° C.) solution of 2-[4-(5-bromo-3-methylpyrid-2-yl)butylamino]-3-nitro-5-(pyrid-3-ylmethyl)pyridine (4.75 g) in methanol (250 ml) containing Raney Nickel (ca. 3 g). The solution was stirred for a further 30 minutes, the catalyst was removed by filtration and the filtrate was concentrated to dryness in vacuo. The residue was chromatographed on silica eluted with 5% v/v methanol in chloroform and then recrystallized from acetonitrile to give the tile compound (2.78 g), m.p. 85°–87° C.

$C_{21}H_{24}BrN_5.1.15\%$ w.w $H_2O$: Requires: C, 58.48; H, 5.74; N, 16.24; Br, 18.53%; Found: C, 58.85; H, 5.86; N, 16.35; Br, 18.71%

(g)
3-[4-(5-Bromo-3-methylpyrid-2-yl)butyl]-6-(pyrid-3-ylmethyl)-3H-1,2,3-Triazolo[5,4-b]pyridine Sodium nitrite (0.33 g) in water (20 ml) was added over 15 minutes to a solution of 3-amino-2-[4-(5-bromo-3-methylpyrid-2-yl)butylamino]-5-(pyrid-3-ylmethyl)pyridine (2.0 g) in molar sulphuric acid (100 ml) stirred at 4° C. The solution was then allowed to warm to room temperature, basified with concentrated ammonium hydroxide solution and extracted with chloroform (3×100 ml). The chloroform extracts were combined, dried over magnesium sulphate, and the solvent removed to give a product which was recrystallised from acetonitrile to give the title compound (1.49 g) as prisms, m.p. 114°–115° C.

$C_{21}H_{21}BrN_6$: Requires: C, 57.67; H, 4.84; N, 19.22; Br, 18.27%; Found: C, 57.69; H, 4.83; N, 19.28; Br, 18.07%

(h)
2-[4-(5-Bromo-3-methylpyrid-2-yl)butylamino]-3-hydroxy-5-(pyrid-3-ylmethyl)pyridine A mixture of 3-[4-(5-bromo-3-methylpyrid-2-yl)butyl]-6-(pyrid-3-ylmethyl)-3H-1,2,3-triazolo[5,4-b]-pyridine (0.6 g) and polyphosphoric acid (ca. 6 g) was heated with stirring at 190°–200° C. for 40 minutes. The cooled residue was dissolved in aqueous ammonium hydroxide to give a solution of ca. pH 8 and extracted with chloroform (4×30 ml). The combined chloroform extracts were dried over magnesium sulphate, concentrated in vacuo and the residue was chromatographed on silica eluted with 7.5% v/v methanol in chloroform and then crystallised under ether to give the title compound (0.12 g), m.p. 164°–166° C.

$C_{21}H_{23}BrN_4O.1.7\%C_2H_5OH+1.5\%H_2O$: Requires: C, 58.20; H, 5.46; N, 12.62; Found: C, 58.12; H, 5.44; N, 12.61

N.M.R. (CDCl$_3$, 250 MHz) assignment, δ(p.p.m.), multiplicity; CH$_2$CH$_2$CH$_2$CH$_2$, 1.80, m; CH$_3$, 2.31, s;

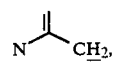

2.80, t; CH$_2$NH, 3.52, t;

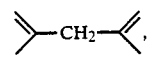

3.74, s; NH/OH, 5.08, br; 4H hydroxypyridyl, 6.40, s; 5H picolyl; ca. 7.30, m; 4H bromopyridyl+4H picolyl+6H hydroxypyridyl, 7.61, m; 6H bromopyridyl+6H picolyl+2H picolyl, 8.40, m.

(i)
2-[4-(5-Bromo-3-methylpyrid-2-yl)butylamino]-5-(pyrid-3-ylmethyl)pyrid-3-yloxyphosphate A mixture of 3-[4-(5-bromo-3-methylpyrid-2-yl)butyl]-6-(pyrid-3-ylmethyl)3H-1,2,3-triazolo[5,4-b]-pyridine (3.9 g) and polyphosphoric acid (ca. 35 g) was heated with stirring at 190°–200° C. for 40 minutes. The cooled residue was dissolved in aqueous ammonium hydroxide to give a solution of ca. pH 8 and extracted with chloroform (4×100 ml). The combined chloroform extracts were dried over magnesium sulphate, concentrated in vacuo to yield 0.6 g title compound (h) m.p. 162°–5° C. The aqueous fraction was evaporated to dryness to yield a pasty residue, which gave on extraction with hot chloroform a further 0.25 g (h) m.p. 163°–164° C. on evaporation. The residue was then heated under reflux with chloroform for 2 hr. and the chloroform solution was chromatographed on silica gel to yield 1.02 g title compound (i) m.p. 110°–112° c.

N.M.R. (DMSO d$_6$ 250 MHz) assignment, δ(p.p.m.), multiplicity; CH$_2$CH$_2$CH$_2$CH$_2$, 1.60, m; CH$_3$, 2.22, s;

2.66, t; CH$_2$NH, 3.27, t;

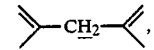

3.73, s; 4H, aminopyridyl+5H picolyl+NH, ~7.28, m; 6H aminopyridyl+4H picolyl, 7.59, m; 4H bromopyridyl, 7.78, m; 8.46+8.47, 6H bromopyridyl+2H picolyl+6H picolyl, m/e 506/8 (m+H)$^+$.

EXAMPLE 2

(a) 5,6,7,8-Tetrahydroquinoline (20 g) was added quickly to sodamide (17.6 g) in liquid ammonia (250 ml) to give a dark red coloured solution. 3-Chloropropylamine hydrochloride (28.9 g) was added in portions over four hours when loss of colour was permanent after which the reaction was stirred for a further 2 hours and then quenched with ammonium chloride (20 g). The liquid ammonia was allowed to evaporate and the residues were partitioned between chloroform and water. The pH was lowered to 6 and the chloroform layer was discarded. The aqueous layer was basified (pH 12–14), and extracted with chloroform, the chloroform extracts were dried, combined, evaporated and the residue was vacuum distilled to give 3-(5,6,7,8-tetrahydroquinol-8-yl) propylamine (7.58 g), b.p. 92°–94° C. at 0.1 mm Hg.

N.M.R. (CDCl$_3$, 250 MHz) assignment, δ(p.p.m.), multiplicity; 6,7-H tetrahydroquinolyl and —CH$_2$CH$_2$CH$_2$NH$_2$, 1.43–2.15, m; 5-H tetrahydroquinolyl and —CH$_2$NH$_2$, 2.75, m; 8-H tetrahydroquinolyl, 2.88, m; 3-H tetrahydroquinolyl, 7.01, m; 4-H tetrahydroquinolyl, 7.32, m; 2-H tetrahydroquinolyl, 8.39, m.

(b)
2-[3-(5,6,7,8-Tetrahydroquinol-8-yl)propylamino]-3-nitro-5-(pyrid-3-ylmethyl)pyridine A mixture of 3-(5,6,7,8-tetrahydroquinol-8-yl)propylamine (4.5 g), 2-chloro-3-nitro-5-(pyrid-3-ylmethyl)pyridine hydrochloride (5 g) and triethylamine (10 ml) was refluxed in ethanol (200 ml) for 7.5 hours. The solvent was removed in vacuo, the residue was dissolved in chloroform and chromatographed on silica in chloroform and later chloroform/methanol 4:1. The fractions containing the product were concentrated to give the title compound as an oil (6.1 g).

(c)
3-Amino-2-[3-(5,6,7,8-tetrahydroquinol-8-yl)propylamino]-5-(pyrid-3-ylmethyl)pyridine Hydrazine hydrate (7 ml) in methanol (25 ml) was added with stirring over 25 minutes to a cooled (5°-10° C.) solution of 2-[3-(5,6,7,8-tetrahydroquinol-8-yl)propylamino-3-nitro-5-(pyrid-3-ylmethyl)pyridine (6.1 g) in methanol (300 ml) containing Raney Nickel (ca. 12 g). The solution was stirred for a further hour at 5° C., the catalyst was removed by filtration and the filtrate was concentrated to dryness in vacuo giving the title compound as an orange oil (theoretical yield assumed) which was used unpurified in the next reaction.

(d)
3-[3-(5,6,7,8-Tetrahydroquinol-8-yl)propyl-6-(pyrid-3-ylmethyl)-3H-1,2,3-triazolo[5,4-b]pyridine Sodium nitrite (1.3 g) in water (60 ml) was added over 25 minutes to a solution of 3-amino-2-[3-(5,6,7,8-tetrahydroquinol-8-yl)propylamino]-5-(pyrid-3-ylmethyl)pyridine (5.5 g) in molar sulphuric acid (250 ml) stirred at 4° C. The reaction mixture was stirred at 4° C. for 50 minutes, then allowed to warm to room temperature, basified with 10 molar sodium hydroxide solution to pH 13 and extracted with chloroform (3×150 ml). The chloroform extracts were combined, dried over magnesium sulphate, and the solvent removed to give a brown oil (6.04 g). The oil was chromatographed on silica in 5% MeOH/chloroform to give the title compound as an oil (3.61 g).

N.M.R. (CDCl₃, 250 MHz) assignment, δ(p.p.m.), multiplicity; 6.7-H tetrahydroquinolyl and —CH₂CH₂CH₂—, 1.60 to 2.25, m; 5-H tetrahydroquinolyl, 2.72, m, 8-H tetrahydroquinolyl, 2.93, m;

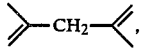

4.19, s; —CH₂CH₂CH₂—, 4.76, m; 3-H tetrahydroquinolyl, 7.00, m; 4-H tetrahydroquinolyl and 5-H pyridyl, 7.27, m; 4-H pyridyl, 7.50, m; 7-H pyridotriazolo, 8.11, s; 2-H tetrahydroquinolyl, 8.34, m; 5-H pyridotriazolo and 2,6-H pyridyl, 8.53, m.

(e)
2-[3-(5,6,7,8-tetrahydroquinol-8-yl)propylamino]-3-hydroxy-5-(pyrid-3-ylmethyl)pyridine A mixture of 3-[3-(5,6,7,8-tetrahydroquinol-8-yl)propyl]-6-(pyrid-3-ylmethyl)-3H-1,2,3-triazolo[5,4-b]pyridine (3.56 g) and polyphosphoric acid (17.5 g) were heated with stirring at 188°–197° C. for 50 minutes. Water (30 ml) was added to the hot residue and, after slight cooling, the solution was basified with aqueous ammonium hydroxide to pH 10 and then extracted with chloroform. The combined chloroform extracts were dried over magnesium sulphate, concentrated in vacuo and the residue was chromatographed on silica eluted with 5% v/v methanol in chloroform to give the title compound as a brown gum (0.68 g). The aqueous portion after extraction, was concentrated to dryness, to give a paste, water (100 ml) was then added, the mixture was refluxed for 1 hour and a brown oil which formed was extracted with chloroform (3×100 ml). The extracts were dried, combined and concentrated to give a further quantity of the title compound as an oil (0.31 g). The two portions of the product were combined, converted to the trihydrochloride with ethanolic HCl and then recrystallised, first from isopropanol and then from isopropanol/methanol to give the title compound as a buff solid (0.5 g).

N.M.R. (CDCl₃, 250 MHz) assignment, δ(p.p.m.), multiplicity; 6,7-H tetrahydroquinolyl and —CH₂CH₂CH₂NH, 1.80, m; 5-H tetrahydroquinolyl, 2.92, m; 8-H tetrahydroquinolyl, 3.30, m; —CH₂CH₂CH₂NH₂, 3.55, m;

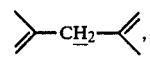

4.09, s; 4-H hydroxypyridyl, 7.18, s; 6-H hydroxypyridyl, 7.46, s; 6-H hydroxypyridyl, 7.46, s; 3-H tetrahydroquinolyl or 5-H pyridyl 7.82, m; 5-H pyridyl or 3-H tetrahydroquinolyl, 7.98, m; 4-H tetrahydroquinolyl, 8.31, d; —CH₂CH₂CH₂NH—, 8.37, m; 4-H pyridyl, 8.43, d; 2-H tetrahydroquinolyl or 6-H pyridyl, 8.65, d; 6-H pyridyl or 2-H tetrahydroquinolyl, 8.80, d; 2-H pyridyl, 8.91, s;

or NH⁺, 11.99, broad s.

EXAMPLE 3

(a)
3-(3-Methyl-5-nitropyrid-2-yl)-3,3-bis(carbethoxy)-propionitrile 2-(Cyanomethyl)malonic acid diethyl ester (G. Casini et al, Ann. Chim. (Rome), 51, 366–74 (1961) (81 g) was reacted with sodium hydride (8.9 g) in tetrahydrofuran at 20° C. 2-Chloro-3-methyl-5-nitropyridine (G. E. Hawkins & A. Roe, J. Org. Chem., 14, 328 (1949)) (58.5 g) was added and the internal temperature was raised to 95°–105° C. (some tetrahydrofuran was distilled off) over 11 hours. The reaction mixture was partitioned between chloroform and water (pH of aqueous phase was lowered to 3), the chloroform extracts were dried and concentrated in vacuo to give an oil (132 g). The oil was distilled under vacuum, the distillate collected at 60°–98° C. (vapour temp.) 0.2 mm Hg was discarded. The residues from the distillation (65 g) were dissolved in chloroform and filtered through a silica column and then concentrated, treated with charcoal and recrystallised from chloroform/petroleum ether (40°–60° C.) to give the title compound (30 g) m.p. 78°–80° C.

(b) 5-Nitro-2-(2-cyanoethyl)-3-methylpyridine 3-(3-Methyl-5-nitropyrid-2-yl)-3,3-bis(carbethoxy)-propionitrile (29.8 g) was dissolved in methanol (1120 ml), molar sodium hydroxide solution (355 ml) was added, the reaction was cooled from 28° C. to room temperature and stirred for 55 minutes. The pH was lowered to 4 by the addition of concentrated hydrochloric acid, the reaction was stirred for 2.75 hr., the pH was then raised to 7 and the methanol was distilled off. The aqueous phase was extracted with chloroform, extracts were dried, filtered and concentrated. The residue was crystallised from chloroform/petroleum ether 40°–60° C. The crude product was treated with charcoal in ethanol and recrystallised from ethanol to give the title compound 10.44 g, m.p. 73°–74° C.

(c) 5-Amino-2-(3-aminopropyl)-3-methylpyridine

Raney nickel (24 g) was added to a stirred solution under nitrogen of 5-nitro-2-(2-cyanoethyl)-3-methyl-pyridine (10.36 g) in ethanol (700 ml). Hydrazine hydrate (13.5 ml) in ethanol (30 ml) was added over 2.75 hr., followed by further additions of Raney nickel (15 g) and hydrazine hydrate (60 ml) over two days which included two periods of eight hours at 50° C. The solution was decanted off, filtered through a hyflo pad and concentrated to dryness to give a green oil (13 g). This oil was chromatographed on silica in ethylacetate/ethanol/0.880 ammonia 15:10:2 to give the title compound as an oil (8.14 g).

N.M.R. (CDCl$_3$, 250 MHz) assignment $\epsilon$(p.p.m.), multiplicity; —CH$_2$NH$_2$, 1.70, broad resonance; —CH$_2$CH$_2$NH$_2$, 1.80, m;

2.23, s; —CH$_2$CH$_2$CH$_2$NH$_2$, 2.75, m;

3.54, broad resonance; 4-H pyridyl, 6.79, s; 6-H pyridyl, 7.88, s.

(d) 2-(3-Aminopropyl)-5-bromo-3-methylpyridine

5-Amino-2-(3-aminopropyl)-3-methylpyridine (8.05 g) in hydrobromic acid (48%, 75 ml) and water (8 ml) wasreacted with cuprous bromide (8.73 g) and copper bronze (0.29 g). A solution of sodium nitrite (5.1 g) in water (8 ml) was added at 5°–8° C. over 40 minutes, the reaction mixture was allowed to stir at 5°–8° C. for one hour and then stirred at room temperature for 3 hours. The cooled reaction mixture was then basified with ammonium hydroxide (70 ml), which was then extracted with chloroform 3×150 ml. The chloroform extracts were then washed with fresh ammonium hydroxide and water (70 ml of each) till no more blue colour was visible in the aqueous layer. Chloroform extracts were dried over magnesium sulphate, filtered and concentrated to dryness to give the title compound (8.2 g) as an amber oil.

N.M.R. (DMSO, 250 MHz): assignment, $\delta$(p.p.m.), multiplicity;

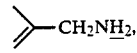

1.48, broad s; —CH$_2$CH$_2$CH$_2$NH$_2$, 1.83, m; —CH$_3$, 2.30, s; —CH$_2$CH$_2$CH$_2$NH$_2$, 2.77, m; 4-H pyridyl, 7.56, s; 6-H pyridyl, 8.40, s.

(e) 2-[3-(5-Bromo-3-methylpyrid-2-yl)-propylamino]-3-nitro-5-(pyrid-3-ylmethyl)pyridine 2-(3-Aminopropyl)-5-bromo-3-methylpyridine (5 g), 2-chloro-3-nitro-5-(pyrid-3-ylmethyl)pyridine hydrochloride (4.45 g) and triethylamine (10 ml) were refluxed together in ethanol (200 ml) for 5.5 hr. A further addition of 2-(3-aminopropyl)-5-bromo-3-methylpyridine (0.5 g) was made and refluxing was continued for a further 2.5 hr. The reaction mixture was then concentrated to dryness giving a yellow oil (13.59 g). The oil was chromatographed on silica in first methanol/chloroform 1:19 increasing the polarity to 1:9. The product was recrystallised from chloroform/petroleum ether (40°–60° C.) to give the title compound (5.11 g), m.p. 105°–106° C.

C$_{20}$H$_{20}$BrN$_5$O$_2$: Requires: C, 54.31; H, 4.56; Br, 18.07; N, 15.83; Found: C, 54.30; H, 4.50; Br, 18.26; N, 15.84

(f) 2-[3-(5-Bromo-3-methylpyrid-2-yl)-propylamino]-3-amino-5-(pyrid-3-ylmethyl)pyridine Hydrazine hydrate (5.3 ml in 25 ml methanol) was added dropwise over 25 minutes to a stirred and cooled suspension under nitrogen of 2-[3-(5-bromo-3-methyl-pyrid-2-yl)propylamino]-3-nitro-5-(pyrid-3-ylmethyl)pyridine (5.07 g) and Raney nickel (10 g) in methanol (600 ml) and ethanol (100 ml) keeping the temperature at 5°–10° C. Reaction was allowed to stir at 5° C. for a further 45 minutes. Raney nickel was filtered off and the filtrate was concentrated to dryness to give an oil which was re-evaporated with n-propanol giving the title compound, theoretical yield, crude product used directly in next reaction.

(g) 3-[3-(5-Bromo-3-methylpyrid-2-yl)propyl]-6-(3-pyridylmethyl)-3H-1,2,3-triazolo[5,4-b]pyridine Sodium nitrite solution (1.02 g in 50 ml water) was added dropwise over 25 minutes to a stirred and cooled solution of 2-[3-(5-bromo-3-methylpyrid-2-yl)-propylamino]-3-amino-5-(pyrid-3-ylmethyl)pyridine (4.7 g) in sulphuric acid (molar, 200 ml) keeping the temperature at 4° C. Reaction was stirred at 4° C. for a further hour and was then left in the fridge overnight and then warmed to room temperature. The reaction mixture was basified to pH 13 with sodium hydroxide solution (10M). Chloroform extraction of the reaction mixture gave the crude product which was then chromatographed on silica in methanol/chloroform 1:19 and then recrystallised from acetonitrile to give the title compound (2.75 g), m.p. 109°–110° C.

C$_{20}$H$_{19}$BrN$_6$: Requires: C, 56.70; H, 4.52; Br, 18.88; N, 19.85; Found: C, 56.87; H, 4.57; Br, 19.05; N, 19.93

(h)
2-[3-(5-Bromo-3-methylpyrid-2-yl)-propylamino]-3-hydroxy-5-(pyrid-3-ylmethyl)pyridine 3-[3-(5-Bromo-3-methylpyrid-2-yl)propyl]-6-(3-pyridylmethyl)-3H-1,2,3-triazolo[5,4-b]pyridine (2.68 g) was added in portions over 15 minutes to hot (190°–200° C.) stirred polyphosphoric acid (10.45 g). The stirred reaction was heated at 190°–200° C. for a further 45 minutes, water (20 ml) was added to the hot reaction mixture, the solution was neutralised with concentrated ammonium hydroxide and allowed to cool. The pH was then raised to 10, chloroform extraction of the aqueous mixture gave a brown solid. This solid was recrystallised from ethanol/ether giving buff crystals (1.64 g). These were chromatographed on silica in methanol/chloroform 1:9, the product was then recrystallised from chloroform/petroleum ether (40°–60° C.) to give the title compound (1.4 g) (off-white crystals), m.p. 141°–143° C.

$C_{20}H_{21}BrN_4O$: Requires: C, 58.12; H, 5.12; Br, 19.33; N, 13.56; Found: C, 58.01; H, 5.15; Br, 19.42; N, 13.53

EXAMPLE 4

A pharmaceutical composition for oral administration is prepared containing

|   |   | % by weight |
|---|---|---|
| A | 2-[4-(5-Bromo-3-methylpyrid-2-yl)butyl-amino]-3-hydroxy-5-(pyrid-3-ylmethyl)-pyridine | 55 |
|   | Dibasic calcium phosphate dihydrate | 20 |
|   | Approved coloring agent | 0.5 |
|   | Polyvinylpyrrolidone | 4.0 |
| B | Microcrystalline Cellulose | 8.0 |
|   | Maize Starch | 8.0 |
|   | Sodium glycollate | 4.0 |
|   | Magnesium Stearate | 0.5 | by mixing together the ingredients A (substituting lactose or microcrystalline cellulose for dibasic calcium phosphate dihydrate if desired), adding a concentrated solution of polyvinylpyrrolidone and granulating, drying and screening the dried granules; adding the ingredients B to the dried granules and compressing the mixture into tablets containing 5 mg, 25 mg or 50 mg of the free base.

EXAMPLE 5

A pharmaceutical composition for injectable administration is prepared by forming a solution of 2-[4-(5-Bromo-3-methylpyrid-2-yl)butylamino]-3-hydroxy-5-(pyrid-3-ylmethyl)pyridine in sterile water to give a 1 to 5% w/w solution. The solution is clarified by filtration and filled into vials which are sealed and sterilised. A suitable vial contains 2 ml of the solution.

What is claimed is:

1. A compound of formula (1):

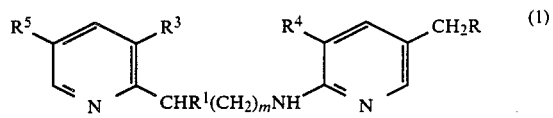

or a pharmaceutically acceptable acid addition salt thereof in which
$R^1$ is hydrogen;
$R^3$ is hydrogen, $C_{1-4}$alkyl, halogen, or amino;
$R^4$ is hydroxy or a phosphate group which is a group of the formula:

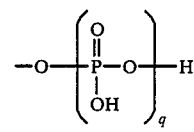

and q is 1 to 3;
$R^5$ is hydrogen, $C_{1-4}$alkyl, halogen, or amino, provided that $R^3$ and $R^5$ are not both hydrogen;
m is 2, 3 or 4; and
R is a 2, 3, or 4-pyridyl or pyridyl N-oxide or N-$C_1$-$C_4$alkylpyridone group optionally substituted by one or two groups selected from $C_{1-4}$alkyl, $C_{1-4}$alkoxy, hydroxy and hydroxymethyl.

2. A compound according to claim 1 wherein $R^1$ is hydrogen.

3. A compound according to claim 2 in which $R^3$ is halogen, $C_{1-4}$alkyl or amino, $R^5$ is hydrogen, halogen or alkyl, and m is 3.

4. A compound according to claim 3 in which $R^3$ is methyl or amino and $R^5$ is bromine.

5. A compound according to claim 1 in which R is 3-pyridyl, 6-methyl-3-pyridyl, 6-methyl-3-pyridyl N-oxide or 6-hydroxymethyl-3-pyridyl.

6. A compound according to claim 1 wherein $R^4$ is hydroxy.

7. A compound according to claim 1 selected from the group consisting of
2-[4-(5-bromo-3-methylpyrid-2-yl)butylamino]-3-hydroxy-5-(pyrid-3-ylmethyl)pyridine
2-[3-(5-bromo-3-methylpyrid-2-yl)propylamino]-3-hydroxy-5-(pyrid-3-ylmethyl)pyridine
2-[4-(5-bromo-3-methylpyrid-2-yl)butylamino]-3-hydroxy-5-(6-hydroxymethyl-pyrid-3-ylmethyl)pyridine
or a pharmaceutically acceptable acid addition salt thereof.

8. A compound according to claim 1 which is 2-[4-(5-bromo-3-methylpyrid-2-yl)butylamino]-5-(pyrid-3-ylmethyl)pyrid-3-yloxyphosphate or a pharmaceutically acceptable acid addition salt thereof.

9. A pharmaceutical composition having histamine $H_1$-antagonist activity which comprises, in an effective amount to produce said activity, a compound according to claim 1 and a pharmaceutically acceptable carrier.

10. A method of blocking histamine $H_1$-receptors which comprises administering to a subject an effective amount to block said receptors of a compound according to claim 1.

* * * * *